United States Patent
Savoia

(10) Patent No.: US 12,311,117 B1
(45) Date of Patent: May 27, 2025

(54) METHOD FOR BIO-PHONON IN PHASE TUNING

(71) Applicant: SavviSound LLC, Jacksonville, NC (US)

(72) Inventor: Lee Savoia, Pensacola, FL (US)

(73) Assignee: SavviSound, LLC, Pensacola, FL (US)

( * ) Notice: Subject to any disclaimer, the term of this patent is extended or adjusted under 35 U.S.C. 154(b) by 0 days.

(21) Appl. No.: 19/040,315

(22) Filed: Jan. 29, 2025

Related U.S. Application Data

(63) Continuation of application No. 19/029,071, filed on Jan. 17, 2025, which is a continuation of application No. 18/678,942, filed on May 30, 2024, now Pat. No. 12,233,217.

(60) Provisional application No. 63/505,412, filed on May 31, 2023.

(51) Int. Cl.
| | |
|---|---|
| *A61M 21/02* | (2006.01) |
| *A61M 21/00* | (2006.01) |
| *G16H 10/20* | (2018.01) |
| *G16H 40/63* | (2018.01) |

(52) U.S. Cl.
CPC ........... *A61M 21/02* (2013.01); *G16H 10/20* (2018.01); *G16H 40/63* (2018.01); *A61M 2021/0027* (2013.01); *A61M 2205/505* (2013.01)

(58) Field of Classification Search
CPC .......... A61M 21/02; A61M 2021/0027; A61M 2205/505; G16H 10/20; G16H 40/63
See application file for complete search history.

(56) References Cited

U.S. PATENT DOCUMENTS

| | | |
|---|---|---|
| 2007/0258329 A1 | 11/2007 | Winey |
| 2009/0312817 A1 | 12/2009 | Hogle et al. |
| 2017/0173262 A1* | 6/2017 | Veltz ................. G16H 20/17 |
| 2018/0017527 A1 | 1/2018 | Generazio |
| 2018/0117274 A1* | 5/2018 | Porges ................. A61M 21/00 |
| 2019/0247662 A1* | 8/2019 | Poltroak ............. A61N 1/0534 |

(Continued)

FOREIGN PATENT DOCUMENTS

WO 2019240622 A1 12/2019

OTHER PUBLICATIONS

International Search Report and Written Opinion issued in App. No. PCT/US2024/031694, dated Sep. 16, 2024, 7 pages.

*Primary Examiner* — Carrie R Dorna
*Assistant Examiner* — Joshua Daryl D Lannu
(74) *Attorney, Agent, or Firm* — Blueshift IP; Robert Plotkin

(57) ABSTRACT

Methods for providing phonon therapy comprise presenting a subject with a plurality of "yes" or "no" questions relating to the subject's personality and/or lifestyle. Each question is assigned to a frequency of about 256.87 Hz, about 288.33 Hz, about 342.88 Hz, about 384.87 Hz, or about 432 Hz. A frequency score is determined for each frequency as the sum of the "yes" answers to the questions that correspond to that frequency. A predominant resonant frequency is identified as the frequency having the highest frequency score, and the subject is exposed to an audio tone having the predominant resonant frequency. The method may be embodied in a computing device comprising a touchscreen and speaker for displaying the questions, receiving the subject's input answer, determining the subject's predominant resonant frequency, and playing the predominant resonant frequency to the subject.

26 Claims, 9 Drawing Sheets

(56) References Cited

U.S. PATENT DOCUMENTS

| | | |
|---|---|---|
| 2019/0373687 A1 | 12/2019 | Williams et al. |
| 2020/0219615 A1* | 7/2020 | Rabin .................... G16H 20/00 |
| 2020/0324076 A1* | 10/2020 | Sarin ........................ H04R 5/04 |
| 2021/0030308 A1* | 2/2021 | Grace .................... A61B 5/486 |

* cited by examiner

METHOD FOR BIO-PHONON IN PHASE TUNING

CROSS-REFERENCE TO RELATED APPLICATIONS

This application is a continuation of prior application Ser. No. 19/029,071, filed Jan. 17, 2025, which is a continuation of prior application Ser. No. 18/678,942, filed May 30, 2024, which claims the benefit of U.S. Provisional Application No. 63/505,412, filed May 31, 2023, which are hereby incorporated by reference herein in their entirety.

BACKGROUND OF THE INVENTION

The present disclosure relates to methods for therapeutic treatment using sound, and more particularly to devices for producing resonant frequencies that are tuned to an individual for use in therapeutic treatment.

Acupuncture's five phases, also known as the five elements or five movements, are a theoretical framework used in traditional Chinese medicine (TCM) to understand the dynamic interrelationships of various phenomena in the body and the natural world. The five phases are Wood, Fire, Metal, Water, and Earth. Each phase represents a different aspect of energy and corresponds to specific organs, seasons, emotions, colors, tastes, and other factors.

According to TCM, the concept of acupuncture meridian blockage refers to an imbalance or obstruction in the flow of Qi (vital energy) along the meridians or energy channels in the body. It is believed that when the Qi becomes blocked or disrupted, it can lead to various health issues or discomfort. The smooth flow of Qi through the meridians is essential for maintaining physical and emotional well-being. However, factors such as stress, poor diet, trauma, emotional disturbances, or environmental influences are thought to disrupt the flow of Qi, resulting in blockages.

A blockage in an acupuncture meridian is seen as an area of reduced Qi circulation or excessive Qi accumulation. This blockage can manifest as symptoms related to the affected meridian or organs associated with it. For example, if there is a blockage in the Lung meridian, it may lead to respiratory issues or imbalances in the corresponding organ's functioning.

Acupuncturests aim to address meridian blockages through the insertion of fine needles into specific acupuncture points along the affected meridians. The intention is to stimulate the flow of Qi, remove blockages, and restore balance and harmony to the body's energy system. Other techniques such as acupressure, herbal remedies, cupping, or moxibustion may also be employed to address meridian blockages.

Singing bowls are another technique that can address meridian blockages. The vibrations produced by singing bowls can penetrate the body, reaching deep tissues and meridian pathways. The resonant frequencies of the bowls can help stimulate and harmonize the flow of Qi within the meridians. Vibrational stimulation can help break up stagnation, disperse blockages, and promote the smooth circulation of energy along the meridians.

Singing bowls are often selected based on their specific tones, frequencies, and qualities. Each bowl's sound corresponds to different energy centers or meridians in the body. By playing specific bowls near or on the affected meridians, an individual can experience restoration in balance and harmony to the energetic flow within the meridians. This can help alleviate blockages and encourage a healthier energy flow.

Quartz crystal bowls are standard bowls which emit a musical note when rubbed with a mallet. Quartz crystals are a type of mineral composed of silicon dioxide ($SiO_2$). Quartz is understood in the general engineering world to be piezoelectric and create energy when compressed. Quartz crystals are valued for their clarity, hardness, and ability to resonate with energy.

Quartz crystals have a unique crystal structure and exhibit piezoelectric properties, meaning they can generate an electric charge in response to applied mechanical stress or pressure. Piezoelectric materials have a unique crystal structure that allows them to exhibit this property. When mechanical force or pressure is applied to a piezoelectric material, such as quartz, it causes a displacement of charged particles within the material. This displacement creates an electric polarization and results in the generation of an electric voltage or potential across the material. When the quartz crystal is struck or rubbed, it begins to vibrate at its natural resonant frequency, creating a sustained and pure sound. The piezoelectric effect helps amplify and maintain these vibrations, contributing to the rich and resonant qualities of the sound produced.

Quartz crystal singing bowls can produce musical notes that correspond to specific frequencies. Quartz singing bowls are typically made from pure quartz crystal or a blend of quartz and other gemstones. When a quartz singing bowl is played by striking or rubbing its rim with a mallet, it produces a rich and resonant sound.

When a quartz crystal is struck, rubbed, or subjected to mechanical pressure, it undergoes vibrations due to the piezoelectric effect. These vibrations generate phonons, which are responsible for the production of sound. The mechanical energy applied to the crystal is transformed into vibrational energy, leading to the emission of sound waves.

Phonons are quanta of vibrational energy that describe the collective vibrational modes or oscillations of atoms or molecules in a material. In the context of sound, phonons represent the vibrational motions that propagate as sound waves through a solid material. This property arises from the arrangement of atoms within the crystal lattice and their ability to undergo vibrations.

Quartz crystals have a unique vibrational resonance that allows them to sustain vibrations for an extended duration. This resonance enhances the sound properties of the crystal. When the crystal is stimulated, the piezoelectric effect amplifies the vibrational energy, resulting in a more pronounced and resonant sound.

The crystalline structure of quartz allows for the propagation of sound waves with minimal distortion. The uniformity and stability of the crystal lattice contribute to the clarity and purity of the sound produced by quartz crystals. The inherent properties of the crystal, such as its density, shape, and composition, influence the specific tonal qualities and frequencies of the emitted sound.

Phonons are responsible for the transmission of sound energy through solids. When a sound wave travels through a solid material, it causes the atoms or molecules within the material to undergo vibrations. These vibrations can be thought of as phonons. Phonons represent discrete packets of vibrational energy associated with specific frequencies and wavelengths.

Traditional methods of stimulating the flow of Qi (e.g., acupuncture, acupressure, herbal remedies, cupping, and moxibustion) commonly require administration by trained professionals, can involve time consuming and invasive procedures, and may require supplies that are not easily accessible. It would be desirable to provide a methods of stimulating Qi flow that can be readily self-administered at the subject's convenience, is non-invasive, and does not require any special components. Self-administration would also promote regular and frequent treatment, and increase the available data for monitoring improvements to health.

SUMMARY OF THE INVENTION

Methods and devices are disclosed for phonon therapy. In one embodiment, a method of phonon therapy of a subject comprises the steps of: determining a predominant resonant frequency of the subject, selected from the group consisting of: about 256.87 Hz, about 288.33 Hz, about 342.88 Hz, about 384.87 Hz, and about 432 Hz; and exposing the subject to an audio composition comprising an audio tone having the predominant resonant frequency.

In another embodiment, a method of phonon therapy of a subject comprises the steps of: presenting the subject with a plurality of questions, each question having a yes or no answer, and each question is assigned to a frequency selected from the group consisting of: about 256.87 Hz, about 288.33 Hz, about 342.88 Hz, about 384.87 Hz, and about 432 Hz; determining a frequency score for each frequency that comprises the sum of the yes answers to the questions that correspond to each frequency; determining a predominant resonant frequency as the frequency having the highest frequency score; and exposing the subject to an audio composition comprising an audio tone having the predominant resonant frequency.

In another embodiment, a device for phonon therapy of a subject comprises a processor, a touchscreen display coupled to the processor, a speaker coupled to the processor, and a computer readable medium coupled to the processor. A plurality of audio compositions comprising an audio tone are stored on the computer readable medium, each audio tone having a frequency selected from the group consisting of: about 256.87 Hz, about 288.33 Hz, about 342.88 Hz, about 384.87 Hz, and about 432 Hz. A plurality of questions are stored on the computer readable medium, each question having a yes or no answer, and each question corresponding to an audio tone. The processor is configured to: display the plurality of questions on the touchscreen display; receive the answer to each question via the touchscreen display; determine a frequency score for each frequency, that comprises the sum of the yes answers that correspond to each frequency; determine a predominant resonant frequency as the frequency having the highest frequency score; and control the speaker to play the audio composition comprising the audio tone having the predominant resonant frequency.

DETAILED DESCRIPTION OF THE INVENTION

Figure 1B:
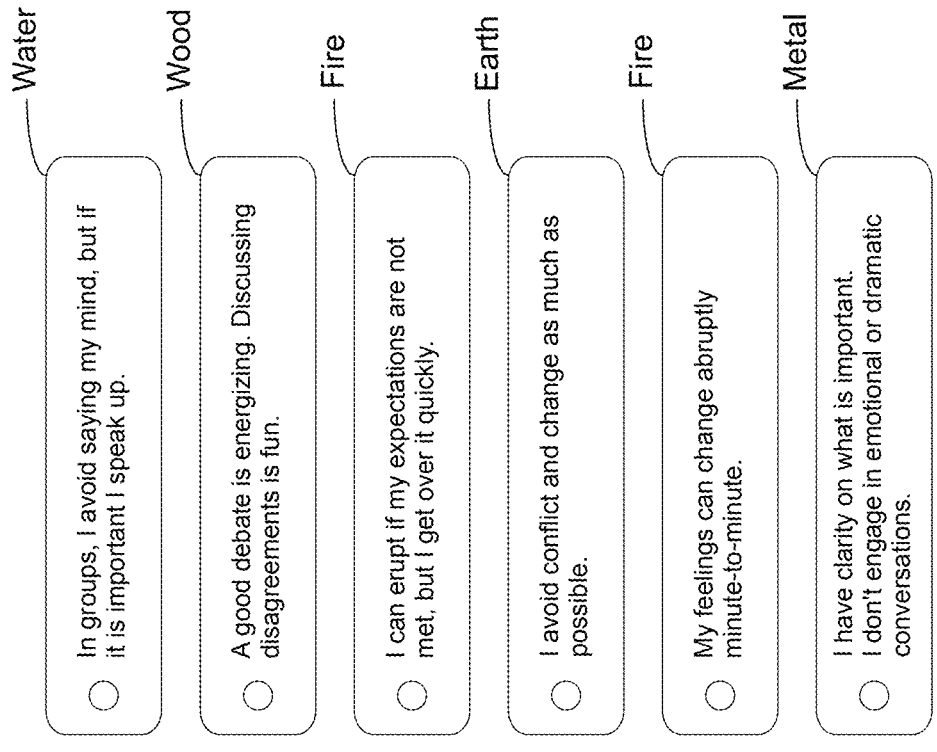
FIGS. 1A-1G are representations of display screens of an embodiment of a mobile application, presenting a series of questions in the category of the subject's personality.
Figure 1A:
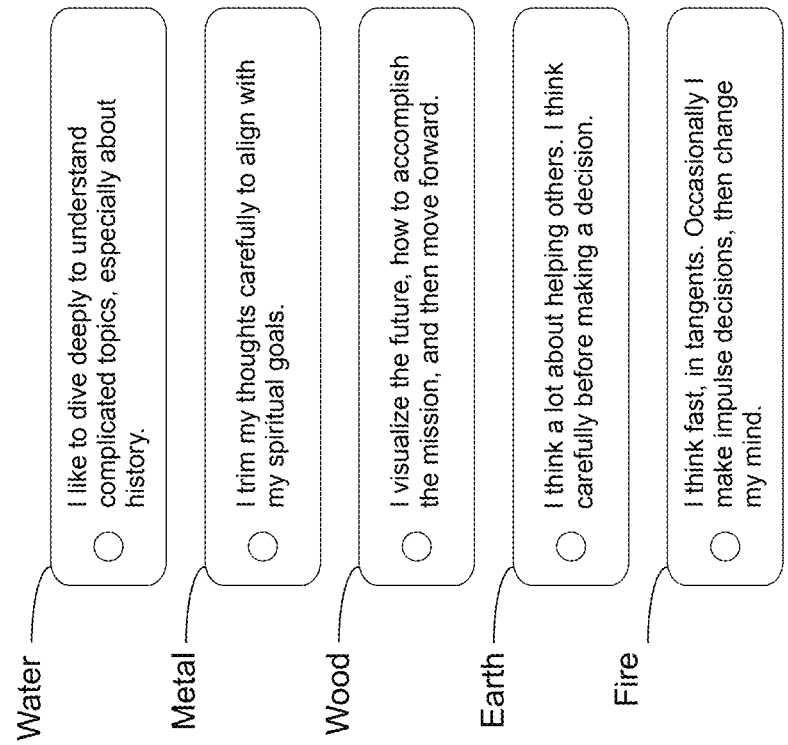
Figure 1D:
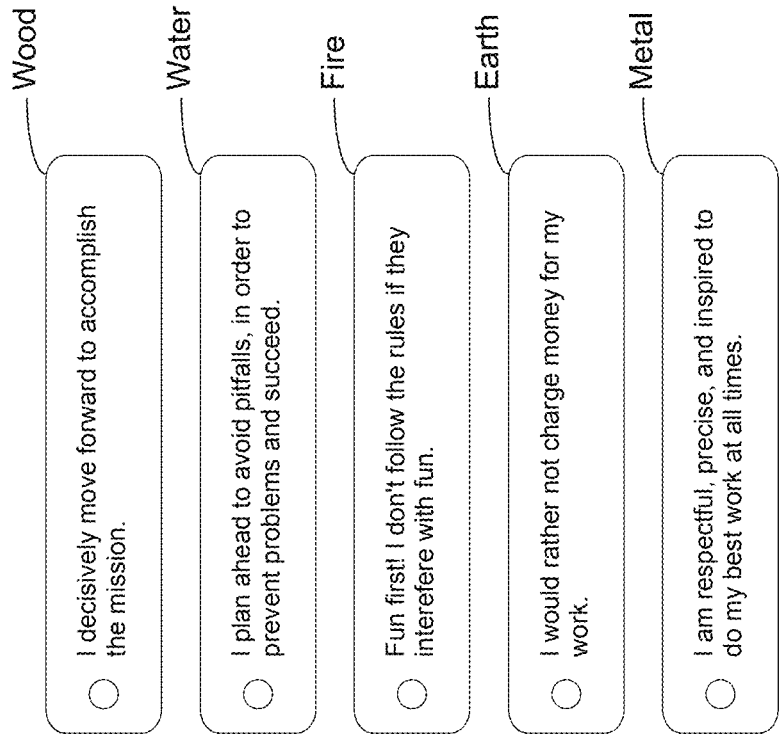
Figure 1C:
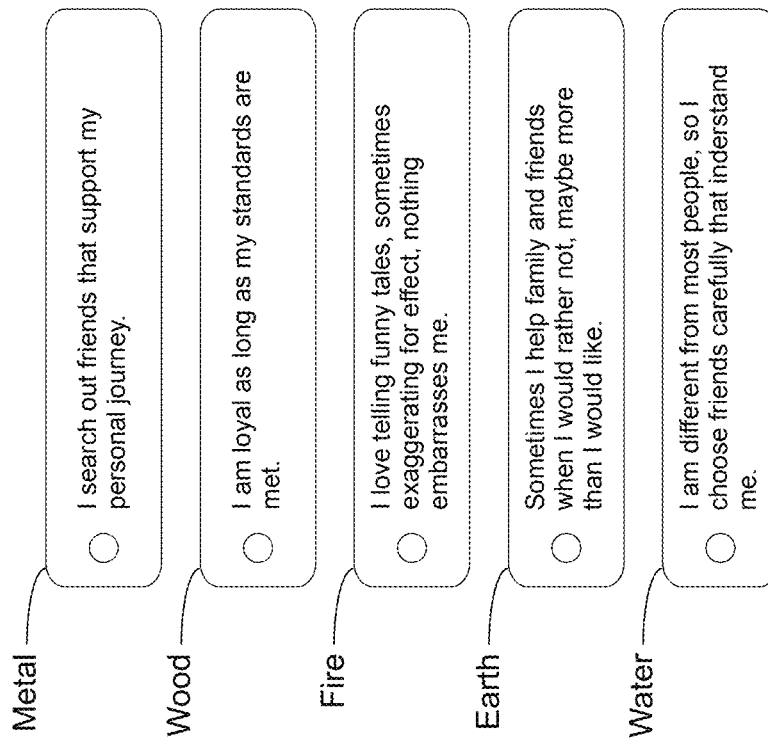
Figure 1F:
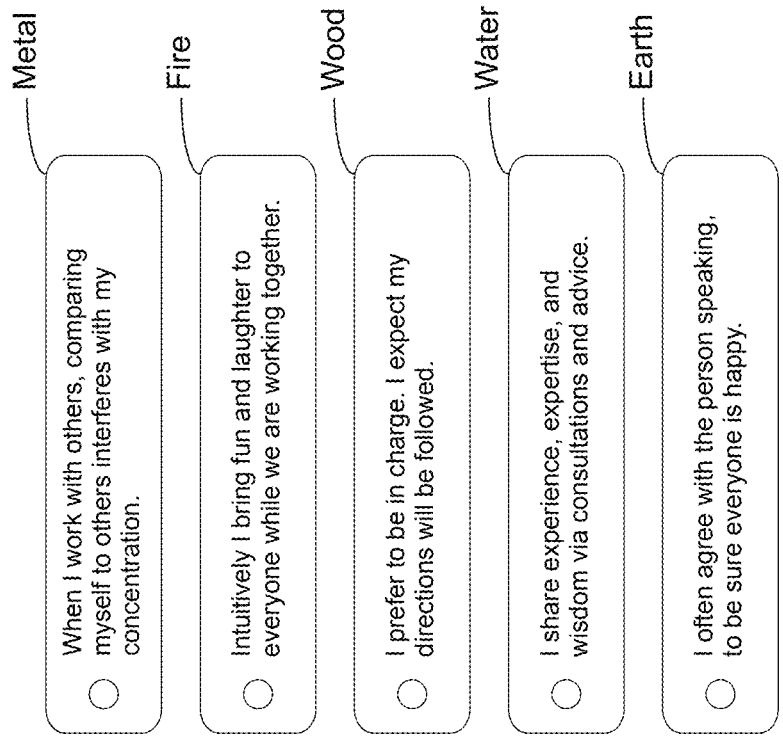
Figure 1E:
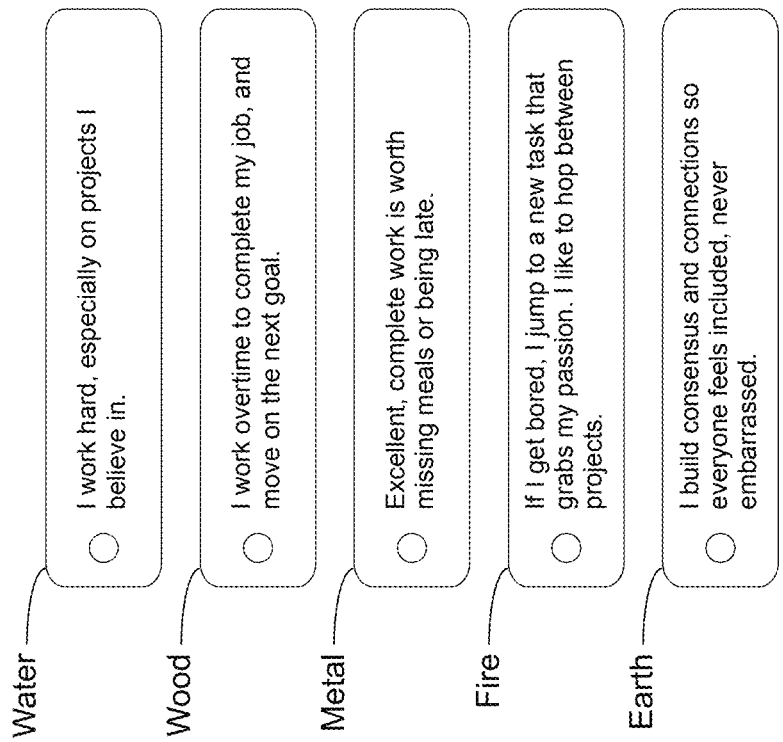
Figure 1G:
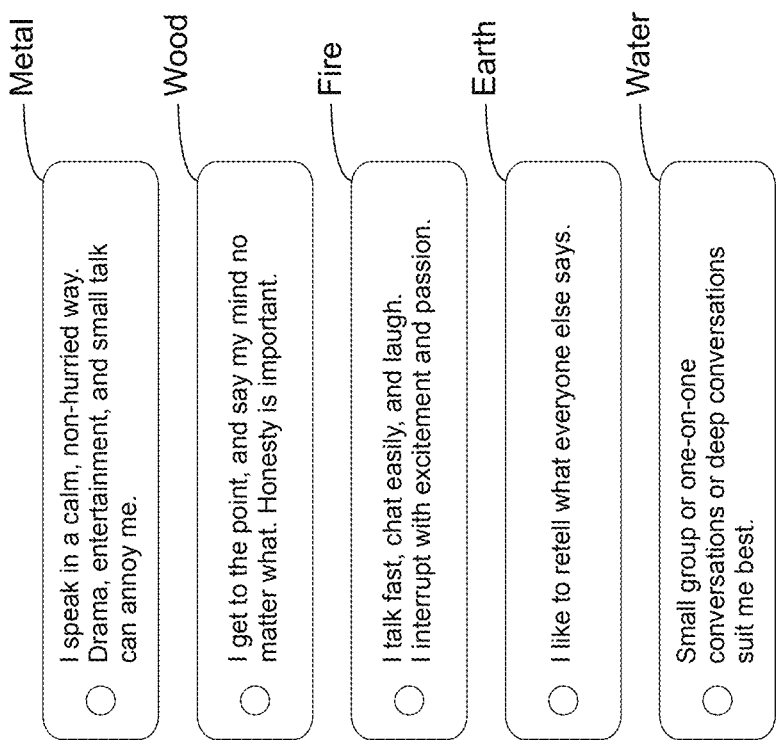
Figure 2B:
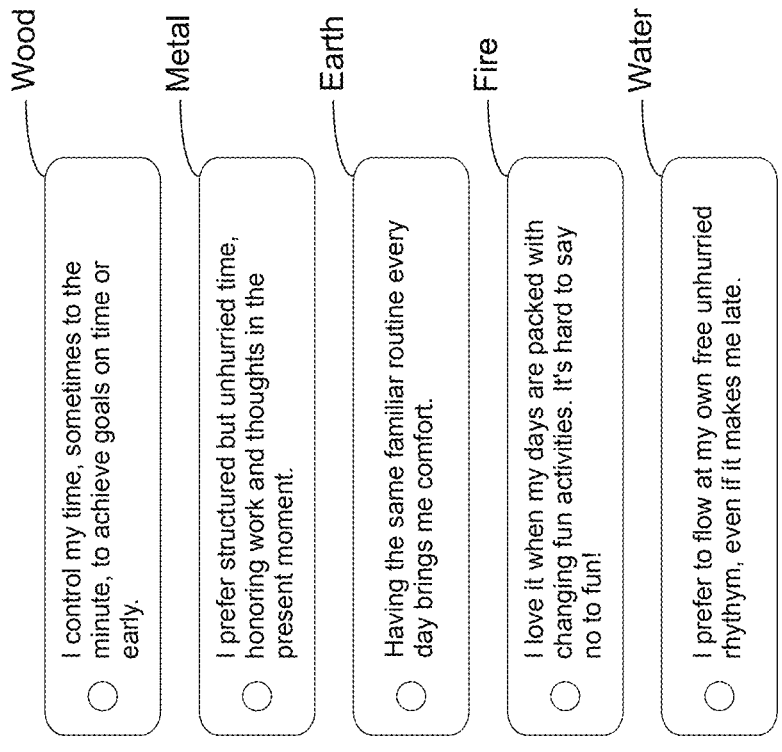
FIGS. 2A-2F are representations of display screens of an embodiment of a mobile application, presenting a series of questions in the category of the subject's lifestyle.
Figure 2A:
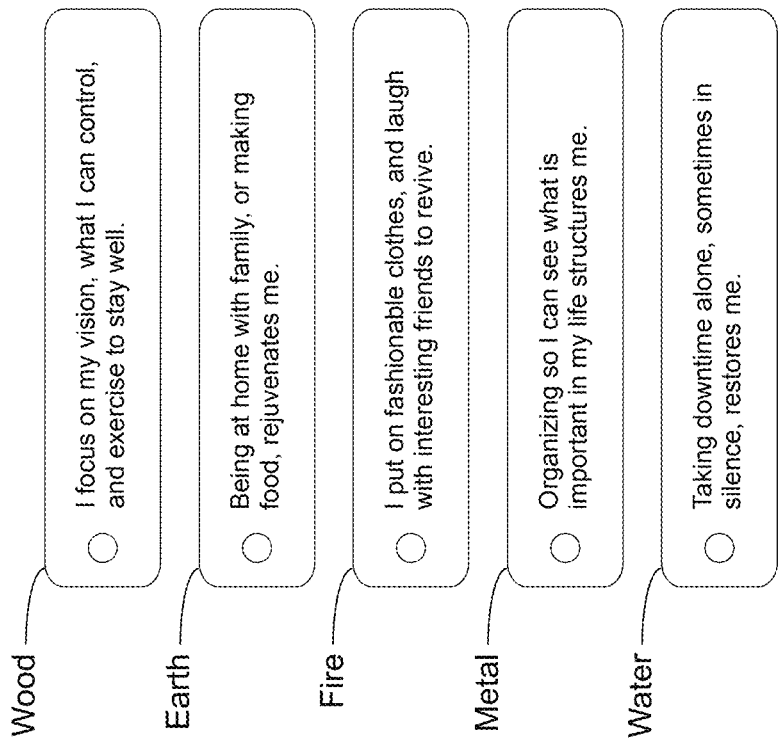
Figure 2D:
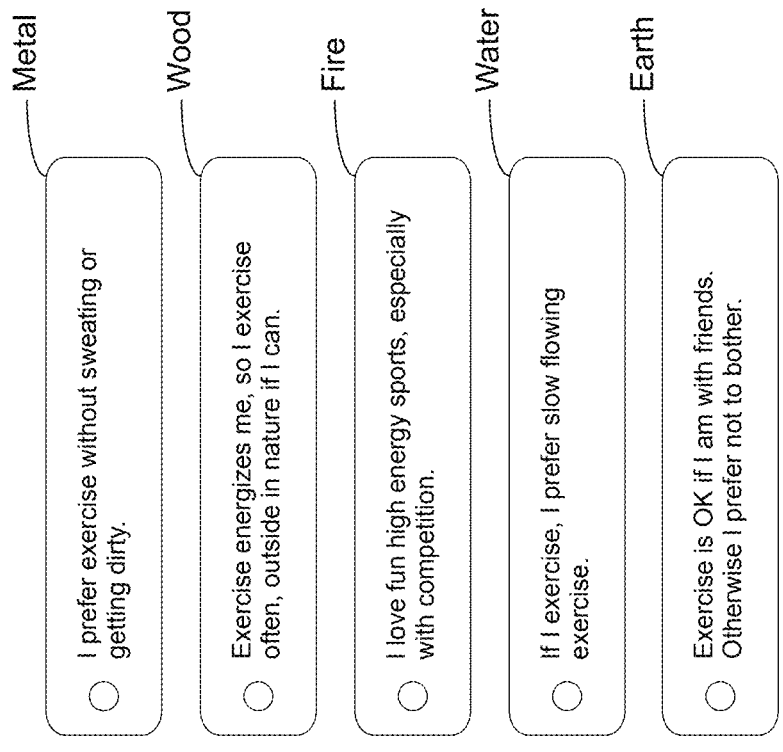
Figure 2C:
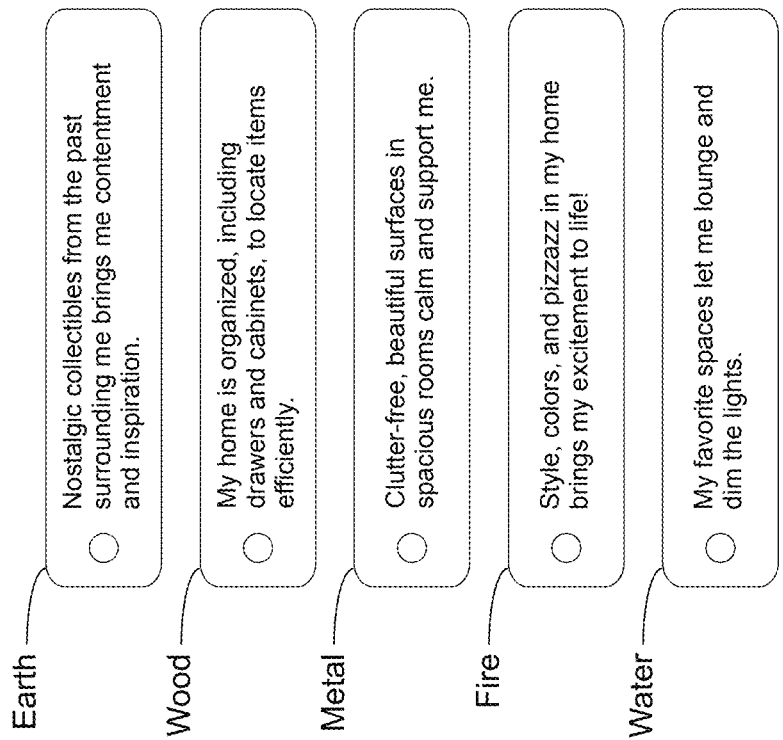
Figure 2F:
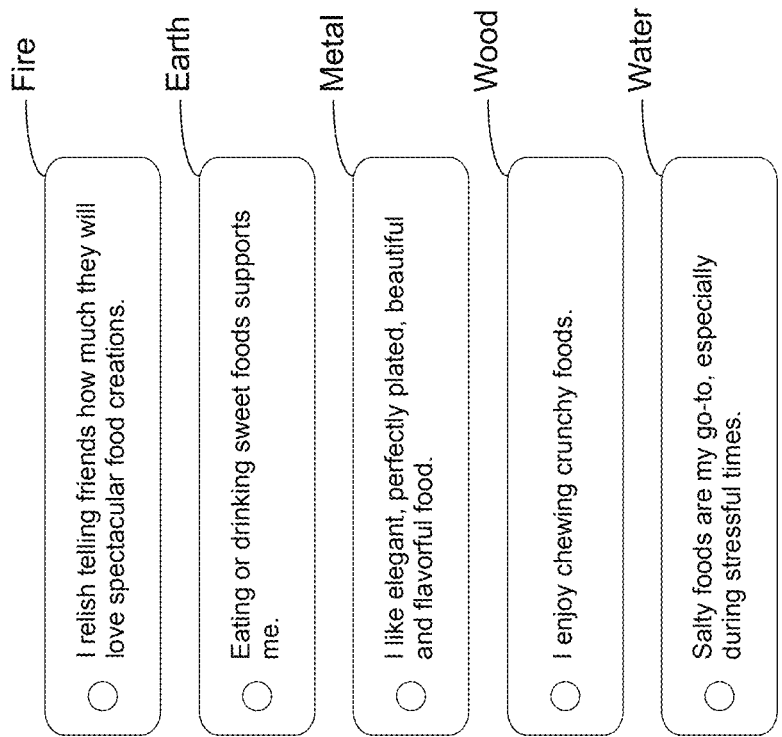
Figure 2E:
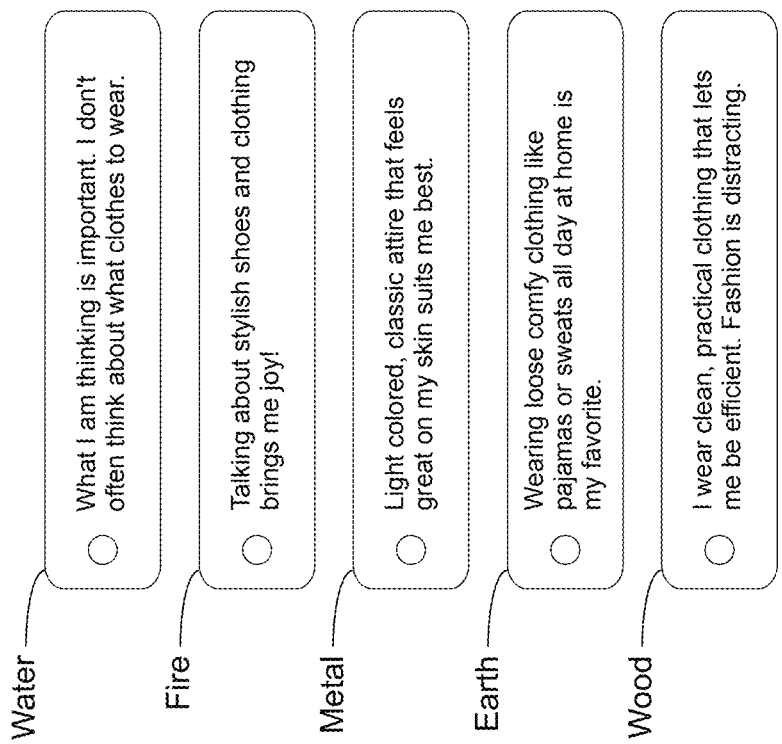

Methods and devices for phonon therapy, or bio-phonon in phase tuning ("BIPT") are described. In one embodiment, the method utilizes quartz crystal singing bowls that can create sounds with frequencies corresponding to the musical notes A, C, G, D, and F. The present invention is not limited to a specific manner in which an individual listens to the sounds created by a quartz crystal singing bowl (such as headphones, speakers, other methods). The present invention also provides a noninvasive therapeutic method that does not require acupuncture needles or other invasive techniques.

The method first involves identifying which of the acupuncture five phases best fits an individual when the individual is in optimal health. This can be determined by questionnaires, online forms, or interviews designed to assess the individual's personality characteristics and lifestyle preferences. This is considered an individual's predominant phase.

The second step involves identifying the corresponding musical note associated with the individual's predominant phase, which is matched to the corresponding frequency for that musical note. Exposure or listening to an individual's predominant resonant frequency is believed to stimulate the flow of Qi through the corresponding meridian energy systems, similarly to acupuncture and other techniques.

The five phases (Wood, Fire, Metal, Water, and Earth) are understood to be interconnected with different aspects of the meridian energy system, and to correspond to different physical attributes and personal characteristics—e.g., specific organs, food and diet preferences, personalities, emotions, seasons, emotions, colors, tastes, and other factors. Each individual comprises a combination of the five phases, with one phase typically dominant.

An individual's predominant phase can be identified by the corresponding personality and lifestyle characteristics that distinguish each phase. Individuals having Wood as the dominant phase are generally characterized by an active, goal oriented, and future driven vision. They organize their time, home and wear clothing such that they accomplish goals efficiently and quickly. They can be abrupt in their conversation in their desire for efficiency. They value saying their mind with complete honesty so can be seen as blunt and rude by others. Control is important to them, and they prefer to be in charge. They are assertive and decisive, which they view as a positive attribute but can come across as angry or causing conflict. They have high standards and only support friends who meet those standards. They view a friend who is not completely honest as lying, and can discard that friend, usually forever. Using muscles gives them energy so they enjoy exercise daily if possible, and enjoy chewing food.

Individuals having Fire as the predominant phase are generally characterized by a desire to celebrate the moment, and seek joy, relationships, and fun. They think and move quickly, hopping, jumping, and bouncing. They like fast fun exercise especially if it is competitive. As they think fast and adapt quickly, they like change. They can make impulsive quick decisions, then change their mind later, which can be hard for others types. Their emotions can fluctuate from moment-to-moment in accordance with their fast-paced nature. Since they are dramatic and passionate, the quick change in emotions from glad to sad, or angry to not angry, can bother other types. They intuitively know how to share their love of life, enjoy being the center of attention making others laugh, and laugh in their everyday conversation. They insist on talking about bright and fashionable clothing and special food concoctions that bring them joy. They speak with passion and drama. Nothing embarrasses them. They are fun followers rather than rule followers, and will quit a project or job when it is no longer exciting.

Individuals having Earth as the predominant phase are generally characterized by nurturing and connecting people, and relate to the past. They organize their time, home and wear clothing comfortably so that they can make homemade nurturing food or gifts for people in their circle. They like to keep things the same without change, which leads them to avoid confrontation and creates a desire for predictability and security. To avoid conflict and change, they will verbally agree when in reality, they do not agree. Out of a desire to nurture and avoid conflict, they can agree to help others when detrimental to themselves. Since their concern is for others, they would prefer to give their work away. Since they think slowly, do not like change, and will not speak up against what someone else has said when they disagree, they can come across as indecisive. They think a lot about the folks and activities they care about which can be interpreted as worry. Since they are concerned with others, in conversation they tell stories about what other people say. When creating community, they avoid conflict, embarrassment, and shame. Exercise is not important to them but they exercise if they have to or if people they care about exercise. Sweets help them during tough times.

Individuals having Metal as the predominant phase honor the present, and the space-in-between moments. Metals are characterized by transforming trauma and grief into understanding and acceptance. They seek to clarify and illuminate what is important, and discard extraneous cluttering distractions such as emotions, fun, and chit-chat small talk. They don't hang on to items from the past. This can make them appear detached and uninterested. Their home, clothing, how they think, even how they put food on their plate, all support minimalizing life to its core. They are precise in how they structure their time, work, and communication. They believe in excellence and value doing things correctly in the moment as well as obtaining the best result, even if this makes the project go overtime. They are on their own journey, keep only friends that support their journey, and prefer to work alone. They like the benefits of exercise without the extraneous sweat which can accompany some forms.

Individuals having Water as the predominant phase are generally characterized by determination, and a perceptive nature with a desire for survival. They listen carefully for danger, plan and prepare for all potential bad outcomes, then undertake any mission, even the most adventurous, with confidence. They work hard on projects if they believe in them. They prefer to flow like water in how they spend time and if they exercise. They prefer spaces that mimic the dark at the bottom of a large body of water, where one is alone and where silence prevails, which is regenerative for them. Anatomically they are related to the adrenals, which regulate body salt, and can crave salt especially during times of stress. They are introspective and independent, prefer anonymity, and quiet in groups, although they speak up if important to them. One-on-one conversation about deep topics suits them. They can be seen wearing wrinkled clothing as their minds are concerned with learning rather than appearing. They seek and acquire deep knowledge. Since they think so deeply, it is hard for them to succinctly explain their knowledge and thoughts, and they can feel misunderstood. They become experts in their field, consulted for advice because of the wisdom they acquire.

In one embodiment, a subject's predominant phase is identified by a questionnaire comprising a series of "yes" or "no" questions in one or more topics relating to the categories of the subject's personality and lifestyle. The questions may be structured as a statement or characterization regarding the subject's personality and/or lifestyle, that is presented for the subject's confirmation. Each question is preferably directed to a characteristic that is specific to a particular phase, such that a "yes" answer uniquely identifies that phase. Questions may also be directed to characteristics that are common to or overlap with more than one phase, such that a "yes" answer identifies multiple phases (i.e. 2, 3, or 4 phases). The phase corresponding to the highest total of "yes" answers is identified as the subject's predominant phase. For example, each "yes" answer may be scored as a single point for the corresponding phase, the sum of the points for each phase determined, and the phase having the highest point total identified as the predominant phase.

In one embodiment, the questionnaire may include one or more questions directed to characteristics that are contradictory to one or more phases, such that a "no" answer tends to exclude those phases. In one embodiment, a question has a "yes" answer that identifies one or more phases, and a "no" answer that tends to exclude one or more phases. The question may be structured such that a "no" answer is scored as a negative of a "yes" answer with respect to one or more phases (e.g., a score of −1 points), or alternatively, may exclude the identification of one or more phases as the predominant phase. In one embodiment, one or more questions are weighted. For example, a weighted "yes" answer may be scored as 2, 3, or more points and/or a weighted "no" answer may be scored as −2, −3, or more negative points.

The questionnaire may comprise questions in the categories of personality and lifestyle topics. Table 1 shows embodiments of question topics in the personality and lifestyle categories. Questions that correspond to each topic are identified by reference and shown in FIGS. 1 and 2. In one embodiment, the questionnaire comprises all 13 question topics of Table 1, and all corresponding questions of FIGS. 1 and 2. The question topics are preferably presented to the subject in random order, such that the personality or lifestyle topics are not substantially grouped together in the questionnaire. In another embodiment, the order of the question topics may be modified such that the initial questions relate to public or outward characteristics, that allow the subject to easily or more comfortably engage with the questionnaire. As the subject proceeds through the questionnaire, the questions increasingly relate to more private and self-revealing characteristics, that may be difficult or uncomfortable for the subject.

TABLE 1

| Questionnaire Category Topics | |
| --- | --- |
| Personality | Lifestyle |
| thought processes (FIG. 1A) | lifestyle priorities (FIG. 2A) |
| personal interaction with others (FIG. 1B) | daily routine (FIG. 2B) |
| perception by others (FIG. 1C) | personal organization (FIG. 2C) |
| self-motivation (FIG. 1D) | exercise (FIG. 2D) |
| work habits (FIG. 1E) | style of dress (FIG. 2E) |
| workplace interaction with others (FIG. 1F) | favorite foods (FIG. 2F) |
| verbal expression (FIG. 1G) | |

The subject may be instructed to answer "yes" to only one question in each topic, or may be allowed to answer "yes"

to two or more questions, if applicable. Allowing multiple "yes" answers in each question topic reflects that individuals are a composite of the five phases, and also alleviates the potential for frustration where the subject believes that multiple questions are true.

Stimulation of an individual's predominant phase improves the flow of Qi through the meridian energy system, and the individual's physical and mental health. Stimulation may be performed by a number of different methods, including acupuncture, acupressure, herbal remedies, cupping, moxibustion, or the like. In a preferred embodiment, the predominant phase is stimulated noninvasively by exposure to sound (bio-phonons).

Each of the five phases is associated with a particular musical note or frequency. Tables 1 and 2 show the musical note frequencies corresponding to each of the five phases. The standard reference pitch (e.g., for tuning musical instruments) is the musical note A above middle C ($A_4$) which is typically set to 440 Hz (A440). The A440 standard was set by the American Standards Association in 1936 and adopted by the International Standards Association in 1955. The frequencies of other notes in the chromatic scale C, G, D, and F are determined relative to this reference pitch. Table 2 shows the musical note frequencies associated with the five phases, using the A440 standard reference pitch.

TABLE 2

Phase Frequencies (A440 Reference Pitch)

| Acupuncture Phase | Musical Note | Tuning Frequency (Hz) |
| --- | --- | --- |
| Wood | $A_4$ | 440 |
| Fire | $C_4$ | 261.63 |
| Metal | $G_4$ | 392 |
| Water | $D_4$ | 293.66 |
| Earth | $F_4$ | 349.23 |

Prior to 1936, there was no standard tuning frequency, and the reference A was commonly tuned between about 432 Hz to 439 Hz. In a preferred embodiment, the reference pitch for the present invention is A432. The frequencies of the notes in the chromatic scale are shown in Table 3.

TABLE 3

Phase Frequencies (A432 Reference Pitch)

| Acupuncture Phase | Musical Note | Tuning Frequency (Hz) |
| --- | --- | --- |
| Wood | $A_4$ | 432 |
| Fire | $C_4$ | 256.87 |
| Metal | $G_4$ | 384.87 |
| Water | $D_4$ | 288.33 |
| Earth | $F_4$ | 342.88 |

For example, the Wood phase is associated with the musical note $A_4$, corresponding to the resonant frequency of 432 Hz. For subjects having Wood as the predominant phase, listening or other exposure to an audio tone having the predominant resonant frequency of 432 Hz returns the subject to a physiological state in which the nascent predominant phase is again predominant. This can result in improvement of physical and mental health issues caused by acupuncture meridian blockage.

The treatment period that is required to provide a health benefit may vary between individuals. In one embodiment, the length of time for exposure to a continuous, uninterrupted audio tone having the subject's predominant resonant frequency is about 5, 10, 15, 20, 25, or 30 minutes per day. In a preferred embodiment, the length of exposure is at least about 15 minutes per day, which is believed to ensure that health benefits are experienced across a wide range of individuals. In addition, treatment for at least thirty consecutive days is believed to ensure that health benefits are observed.

In one embodiment, the subject receives adequate daily hydration during the treatment period. On average, water comprises between about 50% to 70% of body weight. Tuning treatment and the transmittal of sound waves through the body are believed to be most effective when the subject has optimal hydration. A subject's optimal daily water level may be determined as the daily consumption of water in ounces equal to the subject's weight divided by 2. In a preferred embodiment, the subject has an optimal daily water level during the treatment period.

Figure 4:
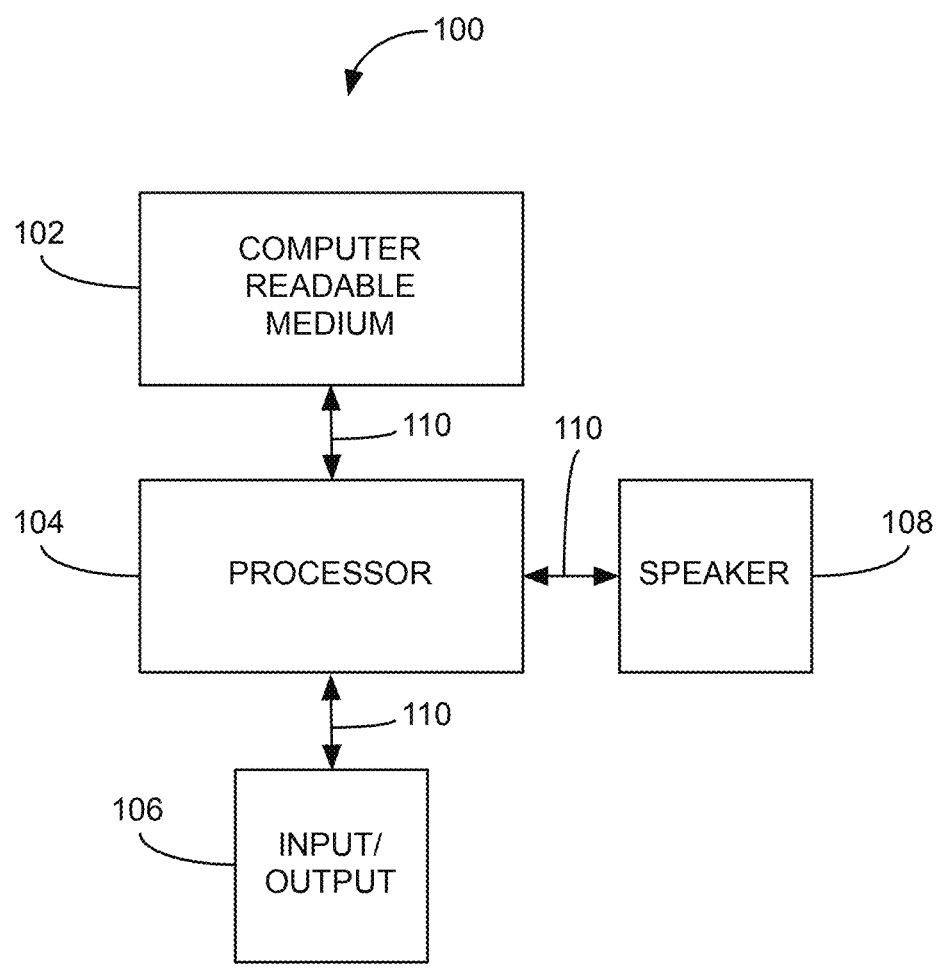
FIG. 4 is a block diagram of a computing device for bio-phonon in phase tuning.

A computing device may be used to determine a subject's predominant phase and provide treatment with the corresponding predominant resonant frequency. An embodiment of a computing device 100 for bio-phonon in phase tuning is shown in FIG. 4. Computing device 100 may comprise separate components, such as a desktop computer with separate peripheral devices (e.g., display and speakers). In a preferred embodiment, computing device 100 is a self-contained, portable audiovisual device, such as a handheld computer, a tablet computer, a mobile phone, laptop computer, tablet device, media player, personal digital assistant (PDA), a multi-function device, a portable gaming device, a headset, or the like.

Computing device 100 comprises a computer-readable medium 102, a processing system 104, an input/output (I/O) system 106, and a speaker 108. These components may be coupled by one or more communication buses or signal lines 110. Computer-readable medium 102 comprises any device or medium that can store code and/or data for use by processor 104, including RAM (e.g., SRAM, DRAM, DDRAM), ROM, flash memory, magnetic and/or optical storage devices, such as disk drives, magnetic tape, CDs (compact disks) and DVDs (digital video discs).

Processor 104 comprises hardware and/or software elements that perform one or more processing functions, such as mathematical operations, logical operations, data manipulation operations, data transfer operations, controlling the reception of user input, controlling output of information to users, or the like. In one embodiment, processor 104 comprises one or more hardware processors, microprocessors, microcontrollers, field programmable gate arrays (FPGAs), application-specified integrated circuits (ASICs), or the like.

Processor 104 runs various software components stored in computer readable medium 102 to perform various functions for computing device 100. In one embodiment, the software components include a suitable operating system, such as iOS, Mac OS, Darwin, RTXC, LINUX, UNIX, OS X, or WINDOWS. The operating system can include various procedures, sets of instructions, software components and/or drivers for controlling and managing general system tasks (e.g., memory management, storage device control, power management, etc.) and facilitates communication between various hardware and software components.

I/O system 106 comprises a display for displaying visual output to the user (e.g., text, graphics, and/or video), and an input device for receiving user input. The display may use any of the various technologies known in the art, including LED (light emitting diode), LCD (liquid crystal display), or LPD (light emitting polymer display) technology. The input device may be any of the various input devices known in the art, including a keyboard, mouse, and/or trackpad. In a preferred embodiment, I/O system 106 is a touch-sensitive or touchscreen display that combines the display and input device functions. The touchscreen display may use any technology suitable for receiving user input in the form of haptic and/or tactile contact (including the movement and release of contact), including capacitive, resistive, infrared, and surface acoustic wave technologies. User contact on the touchscreen display is detected and converted into interaction with user-interface objects (e.g., soft keys and virtual buttons) that are displayed on the touchscreen.

Speaker 108 may be a speaker driver or other device for sound reproduction known in the art, including bookshelf speakers, standing speakers, headphones, earphones, and the like. In a preferred embodiment, speaker 108 radiates sound to the environment and exposes a substantial portion of the subject's body to bio-phonons. Headphone and earphones direct sound specifically to the subject's ears and may limit the benefits of bio-phonon treatment, but are useful where treatment with binaural beats is desired.

One or more applications, modules, and/or sets of instructions may be installed on computing device 100, for the conventional operation of the device. For example, computing device 100 may include modules or instructions stored on computer-readable medium 102 for operation of I/O system 106, such as a touchscreen display. A music player application may be stored on computer readable medium 102, for playing recorded sounds and music (e.g., mp3, wav, or other audio file format known in the art). Other modules include a software timer for timing various events (e.g., duration of tuning treatment), a scheduling module for scheduling and tracking treatments, a hydration reporting module for determination and tracking of the subject's hydration level, and a health reporting module for tracking improvement of the subject's health.

Computing device 100 is configured to present a self-administered questionnaire to the subject, comprising multiple natural language questions in one or more question topics in the categories of the subject's personality and/or lifestyle, as previously described. In one embodiment, the questions comprise one or more question topics of Table 1 and the corresponding questions of FIGS. 1 and 2, and preferably comprise all 13 question topics and corresponding questions. Each question, its correlated phase, and the corresponding resonant frequency are stored on computer readable medium 102.

Processor 104 controls I/O system 106 to display the questions. In one embodiment, the questions are grouped by question topic, and each question topic is displayed in a series of successive screens. FIGS. 1 and 2 show embodiments of the display screens for the questions in each topic of Table 1. Each question is phrased as a statement for confirmation by the subject. In a preferred embodiment, each topic screen comprises at least five questions, with each phase uniquely corresponding to at least one of the questions. FIGS. 1 and 2 indicate the phase (Wood, Fire, Metal Water, or Earth) that is associated with each question. Where a topic has more than five questions, a particular phase may correspond to multiple questions (e.g., Fire in FIG. 1B). The topic screens are presented to the subject in generally random order, such that the topic screens in the personality category and lifestyle category are not substantially grouped together.

The subject is requested to answer "yes" to at least one question in each topic, and uses means appropriate for I/O system 106 to select the questions where the statement is believed to be true—e.g., by representing the question as a virtual button, or providing a option (radio) button, check box, or other graphical control element for each question, as is known in the art. In one embodiment, the subject is requested to answer "yes" to one, two, or three questions in each topic screen. For topic screens consisting of five questions, the subject will generally be requested to answer "yes" to one or two questions, but in some cases may be allowed to answer "yes" to as many as three questions (e.g., the topic screens of FIGS. 1C, and 1D). For topic screens comprising more than five questions (e.g., six questions in FIG. 1B), the subject will generally be requested to answer "yes" to one, two, or three questions.

Each input selection is received by the processor and recorded as a "yes" answer for that question. Where appropriate, each unselected question may be recorded as a "no" answer. In one embodiment, I/O system 106 is a touchscreen that displays the questions as virtual buttons or with option buttons, such as shown in the screens of FIGS. 1 and 2. The subject may select a question to register a "yes" answer, and unselected questions may be registered as a "no" answer.

Each question receiving a "yes" answer is correlated with its phase, and the corresponding resonant frequency for that phase. The processor determines a frequency score for each resonant frequency, that comprises or is based on the total number of "yes" answers correlated to that frequency. For example, each "yes" answer may be scored as a point, and a frequency score is determined for each resonant frequency that comprises or is based on the total number of points corresponding to that frequency. The resonant frequency having the highest frequency score is identified as the subject's predominant resonant frequency.

Figure 3:
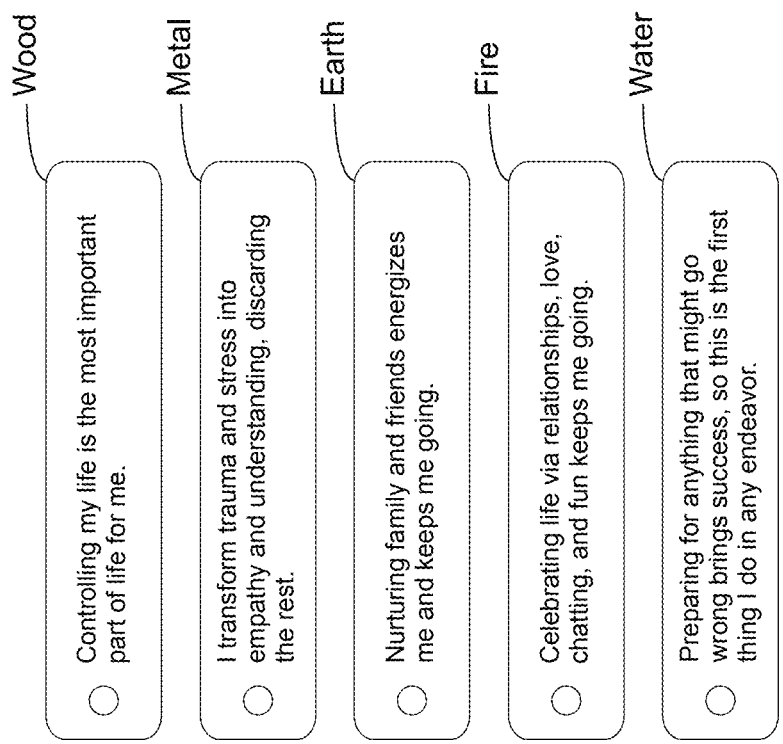
FIG. 3 is a representation of display screen virtual buttons of an embodiment of a mobile application, presenting co-predominant resonant frequency tiebreaker questions.

Other embodiments of the questionnaire may comprise one or more questions where an unselected or "no" answer may be correlated with its associated resonant frequency and a point subtracted from the frequency score, or the associated resonant frequency may be excluded from consideration as the predominant resonant frequency. In another embodiment, the questionnaire comprises one or more weighted questions—e.g., where a "yes" answer is scored as 2 or more points and/or each "no" answer is scored as −2 or more negative points, as appropriate.

Where multiple resonant frequencies are tied for the highest frequency score, computing device 100 may present an additional tiebreaker question topic screen to determine the predominant resonant frequency, or the subject may be considered to have co-predominant resonant frequencies. In one embodiment, the tiebreaker question topic comprises a question for each of the co-predominant resonant frequencies. The subject is requested to answer "yes" to only one question, which identifies the predominant resonant frequency. Examples of tiebreaker topic questions are shown in FIG. 3, represented as display screen virtual buttons, or provided with option buttons. In a preferred embodiment, the tiebreaker question topic consists of only one question for each co-predominant resonant frequency, and does not include any questions corresponding to non-predominant resonant frequencies. For example, where a subject is determined to have the same high frequency scores for Wood ($A_4$ 432 Hz) and Water ($D_4$ 288.33 Hz), the tiebreaker topic screen would only consist of the top two questions shown in FIG. 3.

Processor 104 controls the speaker to play an audio composition comprising an audio tone having the predominant resonant frequency (or audio tones having the co-predominant resonant frequencies). Computing device 100 may comprise an electronic tone generator (not shown) as is known in the art, or recorded audio compositions that comprise the audio tones may be stored on computer readable medium 102 as an electronic audio file, such as mp3, wav, or other audio file format known in the art. In one embodiment, the audio composition is a recording of a musical instrument playing an audio tone having the predominant resonant frequency. In a preferred embodiment, the musical instrument is a quartz crystal singing bowl tuned to the predominant resonant frequency (e.g., played by a mallet rubbing against the bowl).

In one embodiment, the audio composition comprises an audio tone that is a binaural beat. Binaural beats are auditory illusions created by two tones having different frequencies. The two tones are commonly presented to different ears (e.g., through the use of headphones). The listener's brain processes the two tones to create a third tone or beat at the difference of the two frequencies. In one embodiment, the difference in frequencies is about 50 Hz or less, about 30 Hz or less, about 13 Hz or less, about 7 Hz or less, or about 4 Hz or less.

In one embodiment, the audio composition comprises an audio tone and a musical composition. For example, one or more recordings of musical compositions may be stored on computer readable medium 102. The processor controls the speaker to play the audio tone in combination with a musical composition. The musical composition may be in any one of the musical genres, including jazz, rock, classical, and country. In another embodiment, the audio tone may be integrally incorporated in a musical composition.

In one embodiment, computing device 100 also includes a timer module, that is configured to control the duration of the tuning treatment. The timer may be initiated when the audio composition begins playing, and may play the audio composition for a duration or time period set by the timer. The time period may be preset, or the user may be prompted to set a time period for the timer. In a preferred embodiment, the timer module is programmed for exposure to the audio composition for a period of at least about 15 minutes. Computing device 100 may also track and store the subject's daily tuning treatment time and usage data. Computing device 100 may also be configured to produce a signal marking the start and/or end of the audio composition and tuning treatment period. In one embodiment, an audible signal (e.g, a bell sound) is played at the start and end of the audio composition.

In one embodiment, computing device 100 also includes a scheduling module, that is configured to schedule and track tuning treatments. Processor 104 is configured to receive a time and/or date schedule input via I/O system 106 (e.g., a touchscreen). In another embodiment, a predetermined time/date schedule (e.g., daily at a specific time) is stored on computer readable medium 102. Processor 104 controls speaker 108 to play the audio composition according to the time/date schedule and/or controls I/O system 106 to display a reminder for tuning treatment according to the time/date schedule. In another embodiment, processor 104 is configured to record the time/date at which the audio composition is played and/or the duration of the treatment period, and to control I/O system 106 to display the number of times an audio composition is played and/or the duration of the treatment period over time.

In one embodiment, computing device 100 also includes a hydration reporting module, that is configured to track the subject's self-reported hydration level. Computing device 100 prompts the subject to enter his/her weight and daily hydration level, which may be input via I/O system 106 (e.g., touchscreen). Processor 104 is configured to receive the subject's weight and determine an optimal daily hydration level in ounces as the subject's weight divided by 2, and to control I/O system 106 to display the volume (e.g., ounces) of the subject's daily volume of water consumption and/or the volume relative to the subject's optimal daily hydration level over time. The daily volume and/or relative volume of water consumption may also be displayed relative to the corresponding daily tuning treatments over time.

In one embodiment, computing device 100 also includes a health reporting module, that is configured to track the subject's change in physical and/or mental health status. Computing device 100 periodically (e.g., daily, monthly, etc.) prompts the subject to enter his/her self-reported improvement in physical health, mental health, and/or quality of life. In a preferred embodiment, the subject is requested to enter a numerical value for percentage improvement, or to choose between a series of preselected values (e.g., 20%, 40%, 60%, 80%, or 100% improvement). Processor 104 is configured to receive the subject's physical health, mental health, and/or quality of life improvement, and to control I/O system 106 to display the average improvement over time. In one embodiment, the health reporting module is also configured to receive the subject's comments regarding his/her physical and mental health and quality of life, and to track those comments over time. In another embodiment, the periodically reported improvement in physical health, mental health, and/or quality of life (or the running average improvement) may also be displayed relative to the corresponding daily tuning treatments over time. In yet another embodiment, the subject's comments may be tracked by date and/or time, and displayed relative to the corresponding daily tuning treatments over time.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

Bio-Phonon Tuning

The phases and corresponding predominant resonant frequencies were determined for 13 subjects, using a questionnaire comprising question topics and questions similar to those set forth in FIGS. 1 and 2, and described herein. Nine subjects received daily tuning for a treatment period of 1 month. Tuning comprised exposure to an audio composition comprising a continuous audio tone having the subject's predominant resonant frequency. The audio tones were generated by crystal singing bowls having the appropriate frequencies, which were recorded as electronic sound files and stored on the subject's mobile device (e.g., mobile phone). The audio compositions were played for a period of at least about 15 minutes, either directly from the mobile device speaker (without headphones or earphones) or transmitted from the mobile device to a remote speaker. The beginning and end of each 15-minute period was indicated by a bell sound. In one instance (Table 3, Subject 8), the audio composition was played on a remote device and transmitted to the subject's mobile phone.

Four subjects were placed in a control placebo group, that listened to recordings of silence without any audio tone, and were told that the audio tone was subaudible. The beginning and end of each 15-minute period of silence was indicated by a bell sound.

Twelve of the subjects received optimal hydration—i.e. daily consumption of water equal to their (body weight)/2 in ounces. One subject in the placebo group did not receive optimal hydration, and served as a hydration control.

Example 2

Tuning Treatment Results

During the course of tuning treatment, the subjects self-reported the status of their physical health, mental health, and quality of life as a percentage improvement or decline (regression). All subjects that received tuning treatment reported improvement in their Physical Health, Mental Health, and Quality of Life, as shown in Table 3.

TABLE 3

Improvement of Subjects Receiving Tuning

| Subject | Physical Health | Mental Health | Quality of Life | Overall Impact |
|---|---|---|---|---|
| 1 | 10% | 30% | 30% | n/a |
| 2 | 80% | 80% | 80% | 50% |
| 3 | 80% | 80% | 50% | 80% |
| 4 | 30% | 30% | 80% | 50% |
| 5 | 15% | 30% | 30% | 30% |
| 6 | 80% | 75% | 80% | 75% |
| 7 | 80% | 80% | 80% | 90% |
| 8 | 10% | 10% | 10% | 10% |
| 9 | 80% | 80% | 80% | 80% |

It is commonly recognized in medical care, that treatment with a placebo may result in perceived improvement of as much as 30%. Almost all subjects reported an improvement of at least 30% in at least one category of Physical Health, Mental Health, and/or Quality of Life, with the majority of subjects reporting a significant improvement of 50% or greater in at least one health category. Subjects receiving tuning experienced a median/average improvement of: 80%/52% Physical Health, 75%/55% Mental Health, 80%/58% Quality of Life, and 63%/58% Overall Impact on Life.

Most subjects receiving tuning reported some relief of existing medical conditions, such as reduction or other improvement of chronic pain, arthritis, high blood pressure, weight gain, and insomnia. All subjects receiving tuning experienced improvement of mental health, such as reduction of mood swings, reduced irritability, improvement in calmness, relaxation, and sleep, improved motivation, positive outlook and activity, and improvement in general happiness.

Subjects 1 and 8 voluntarily stopped and restarted daily tuning treatments during the treatment period. These subjects experienced the least improvement in Physical Health, Mental Health, and Quality of Life. However, the subjects still reported improvement while receiving tuning treatment. Subject 1 experienced improvement in sleep and mental health during tuning treatment, regressed after tuning treatment was stopped (insomnia, increased irritability, and reduced motivation and activity), and improved again a few days after tuning treatment was restarted. Subject 8 experienced improvement of arthritis, including range of motion and sensation, and in general mental health and quality of life. The improvements reversed after tuning treatment was stopped for 3 days, and returned 2 days after tuning treatment was restored.

In contrast to the subjects that received tuning treatment, the subjects in the placebo group reported either 10% improvement or no improvement in Physical Health, Mental Health, and Quality of Life. No significant difference was observed in placebo group subjects with or without hydration, demonstrating that the reported improvements in physical and mental health are not due to hydration alone.

Although the invention has been described in detail with reference to preferred embodiments, variations and modifications exist within the scope and spirit of the invention as described and defined in the following claims.

What is claimed is:

1. A non-transitory computer-readable medium storing computer instructions for causing a processor to perform a method for phonon therapy of a subject, the method for use with a plurality of audio compositions, each of the plurality of audio compositions comprising an audio tone having a corresponding distinct frequency, whereby the plurality of audio compositions comprises audio tones corresponding to a plurality of distinct frequencies;

the method comprising:
displaying a plurality of questions on a display, each of the plurality of questions having a yes or no answer, and each of the plurality of questions corresponding to an audio tone with a frequency in the plurality of distinct frequencies;
receiving an answer to each question via an input device;
determining a frequency score for each frequency in the plurality of audio compositions, that comprises a sum of the yes answers that correspond to that frequency;
determining a predominant resonant frequency as the frequency having the highest frequency score; and
controlling a speaker to play an audio composition in the plurality of audio compositions comprising an audio tone having the predominant resonant frequency.

2. The non-transitory computer-readable medium of claim 1, wherein each of the plurality of audio compositions comprises an audio tone having a frequency selected from the group consisting of:
about 256 Hz;
about 288 Hz;
about 342 Hz;
about 384 Hz;
about 432 Hz.

3. The non-transitory computer-readable medium of claim 1, wherein each audio tone in the plurality of audio compositions comprises a recording of a musical instrument playing a note having the frequency of that audio tone.

4. The non-transitory computer-readable medium of claim 3, wherein the musical instrument comprises a quartz singing bowl.

5. The non-transitory computer-readable medium of claim 1, wherein the audio composition comprises the audio tone and a musical composition.

6. The non-transitory computer-readable medium of claim 1, wherein the processor is configured to control the speaker to play the audio composition for a period of at least 15 minutes.

7. The non-transitory computer-readable medium of claim 1, wherein the processor is configured to receive a time period, and to control the speaker to play the audio composition for the received time period.

8. The non-transitory computer-readable medium of claim 1, wherein the processor is configured to receive a time schedule via the input device, and to control the speaker to play the audio composition according to the received time schedule.

9. The non-transitory computer-readable medium of claim 1, wherein the processor is configured to record times at which an audio tone in the audio tones in the plurality of audio compositions is played; and to display a number of times the audio tone is played.

10. The non-transitory computer-readable medium of claim 1, wherein the subject has a daily water consumption, and wherein the processor is configured to receive the subject's daily water consumption via the display, and to display the subject's daily water consumption over time.

11. The non-transitory computer-readable medium of claim 10, wherein the subject has a weight, and the processor is configured to receive the subject's weight via the display and determine the subject's optimal daily hydration level in ounces as the subject's weight divided by 2; and wherein the processor is configured to display the subject's daily water consumption over time relative to the subject's optimal daily hydration level.

12. The non-transitory computer-readable medium of claim 1, wherein the subject has a self-reported improvement in health, and the processor is configured to receive a numerical value for percentage improvement in health, and wherein the processor is configured to display an average percentage improvement in health over time.

13. The non-transitory computer-readable medium of claim 1, wherein the method further comprises:
   periodically prompting the subject to enter a self-reported improvement in mental health and quality of life;
   receive numerical values for percentage improvement in mental health and quality of life; and
   displaying average improvements in mental health and quality of life over time.

14. A method, performed by a processor, of phonon therapy of a subject, the method for use with a plurality of audio compositions, each of the plurality of audio compositions comprising an audio tone having a corresponding distinct frequency, whereby the plurality of audio compositions comprises audio tones corresponding to a plurality of distinct frequencies;
   the method comprising:
      displaying a plurality of questions to the subject on a display, each of the plurality of questions having a yes or no answer, and each of the plurality of questions corresponding to an audio tone with a frequency in the plurality of distinct frequencies;
      receiving, via an input device, the subject's answers to each question;
      determining a frequency score for each frequency in the plurality of audio compositions, that comprises a sum of the yes answers that correspond to that frequency;
      determining a predominant resonant frequency as the frequency having the highest frequency score; and
      controlling a speaker to play an audio composition in the plurality of audio compositions comprising an audio tone having the predominant resonant frequency.

15. The method of claim 14, wherein each of the plurality of audio compositions comprises an audio tone having a frequency selected from the group consisting of:
   about 256 Hz;
   about 288 Hz;
   about 342 Hz;
   about 384 Hz;
   about 432 Hz.

16. The method of claim 14, wherein each audio tone in the plurality of audio compositions comprises a recording of a musical instrument playing a note having the frequency of that audio tone.

17. The method of claim 16, wherein the musical instrument comprises a quartz singing bowl.

18. The method of claim 14, wherein the audio composition comprises the audio tone and a musical composition.

19. The method of claim 14, wherein the processor is configured to control the speaker to play the audio composition for a period of at least 15 minutes.

20. The method of claim 14, wherein the processor is configured to receive a time period, and to control the speaker to play the audio composition for the received time period.

21. The method of claim 14, wherein the processor is configured to receive a time schedule via the input device, and to control the speaker to play the audio composition according to the received time schedule.

22. The method of claim 14, wherein the processor is configured to record times at which an audio tone in the plurality of audio compositions is played; and to display a number of times the audio tone is played.

23. The method of claim 14, wherein the subject has a daily water consumption, and wherein the processor is configured to receive the subject's daily water consumption via the display, and to display the subject's daily water consumption over time.

24. The method of claim 23, wherein the subject has a weight, and the processor is configured to receive the subject's weight via the display and determine the subject's optimal daily hydration level in ounces as the subject's weight divided by 2; and wherein the processor is configured to display the subject's daily water consumption over time relative to the subject's optimal daily hydration level.

25. The method of claim 14, wherein the subject has a self-reported improvement in health, and the processor is configured to receive a numerical value for percentage improvement in health, and wherein the processor is configured to display an average percentage improvement in health over time.

26. The method of claim 14, further comprising:
   periodically prompting the subject to enter a self-reported improvement in mental health and quality of life;
   receive numerical values for percentage improvement in mental health and quality of life; and
   displaying average improvements in mental health and quality of life over time.

* * * * *